United States Patent
Takayama

(10) Patent No.: US 8,274,558 B2
(45) Date of Patent: Sep. 25, 2012

(54) ELECTRONIC ENDOSCOPE SIGNAL-PROCESSING DEVICE AND ELECTRONIC ENDOSCOPE SYSTEM

(75) Inventor: Shinichi Takayama, Tokyo (JP)

(73) Assignee: Hoya Corporation, Tokyo (JP)

( * ) Notice: Subject to any disclaimer, the term of this patent is extended or adjusted under 35 U.S.C. 154(b) by 677 days.

(21) Appl. No.: 12/238,855

(22) Filed: Sep. 26, 2008

(65) Prior Publication Data
US 2009/0109284 A1  Apr. 30, 2009

(30) Foreign Application Priority Data
Oct. 29, 2007  (JP) .................................. 2007-280030

(51) Int. Cl.
A62B 1/04  (2006.01)
(52) U.S. Cl. ................. 348/65; 348/45; 348/72; 348/77; 600/101
(58) Field of Classification Search .................... 348/45, 348/65, 72, 77; 600/101
See application file for complete search history.

(56) References Cited

U.S. PATENT DOCUMENTS

| | | | | |
|---|---|---|---|---|
| 5,233,416 A * | 8/1993 | Inoue | | 348/70 |
| 5,751,261 A * | 5/1998 | Zavracky et al. | | 345/55 |
| 6,602,186 B1 * | 8/2003 | Sugimoto et al. | | 600/126 |
| 6,821,245 B2 * | 11/2004 | Cline et al. | | 600/160 |
| 6,937,269 B2 * | 8/2005 | Sugimoto et al. | | 348/74 |
| 6,956,602 B2 * | 10/2005 | Higuchi et al. | | 348/65 |
| 7,009,639 B1 * | 3/2006 | Une et al. | | 348/223.1 |
| 7,123,288 B2 * | 10/2006 | Abe et al. | | 348/65 |
| 7,341,557 B2 * | 3/2008 | Cline et al. | | 600/160 |
| 7,356,102 B2 * | 4/2008 | Morton et al. | | 375/345 |
| 7,713,192 B2 * | 5/2010 | Murata | | 600/179 |
| 7,722,534 B2 * | 5/2010 | Cline et al. | | 600/160 |
| 2002/0035330 A1 * | 3/2002 | Cline et al. | | 600/476 |
| 2005/0065406 A1 * | 3/2005 | Cline et al. | | 600/160 |
| 2006/0178565 A1 | 8/2006 | Matsui et al. | | |
| 2006/0211915 A1 * | 9/2006 | Takeuchi et al. | | 600/109 |
| 2007/0040906 A1 * | 2/2007 | Iketani | | 348/69 |
| 2007/0093691 A1 | 4/2007 | Kobayashi | | |
| 2007/0153542 A1 * | 7/2007 | Gono et al. | | 362/574 |
| 2007/0183162 A1 * | 8/2007 | Higuchi | | 362/458 |
| 2008/0228037 A1 * | 9/2008 | Cline et al. | | 600/160 |
| 2010/0179385 A1 * | 7/2010 | Murata | | 600/109 |
| 2010/0198010 A1 * | 8/2010 | Cline et al. | | 600/109 |
| 2010/0210904 A1 * | 8/2010 | Cline et al. | | 600/109 |

FOREIGN PATENT DOCUMENTS

JP  2006-061620 A  3/2006
JP  2006-239206 A  9/2006

OTHER PUBLICATIONS

English language Abstract JP 2006-061620 A.
English language Abstract JP 2006-239206 A.

* cited by examiner

Primary Examiner — Backhean Tiv
(74) Attorney, Agent, or Firm — Greenblum & Bernstein, P.L.C.

(57) ABSTRACT

An electronic endoscope system is provided that includes an RGB transformer, an R-signal amplifier, and a GB-signal amplifier. The RGB transformer transforms image signals to RGB signals. The R-signal amplifier changes the amplitude of the R signals of the RGB signals to a predetermined gain value. The GB-signal amplifier nonlinearly changes the amplitude of the G signals and B signals of the RGB signals.

4 Claims, 3 Drawing Sheets

ELECTRONIC ENDOSCOPE SIGNAL-PROCESSING DEVICE AND ELECTRONIC ENDOSCOPE SYSTEM

BACKGROUND OF THE INVENTION

1. Field of the Invention

The present invention relates to signal-processing for an electronic endoscope system.

2. Description of the Related Art

There is known an electronic endoscope system that uses narrow band illumination to obtain a spectral image of a particular band for enhancing features such as blood vessels, lesioned areas, and the like, as disclosed in Japanese Unexamined Patent Publication No. 2006-061620. However, the system requires a specialized light source. Thus, this prior art structure raises the cost of the system and is at a disadvantage in carrying out the simultaneous observation of a normal endoscopic image taken with white light. On the other hand, in Japanese Unexamined Patent Publication No. 2006-239206, a spectral image is emulated from the white light by applying a matrix corresponding to the above-mentioned narrow band, to a color transformation matrix which is normally used in image processing.

SUMMARY OF THE INVENTION

However, the image processing disclosed in Japanese Unexamined Patent Publication No. 2006-239206 is complicated, and moreover, it is difficult to emulate a desired spectral image with a linear transformation. Therefore, features of a target for observation, such as a lesion, may not be sufficiently enhanced. For example, in endoscopy, the lesion may be identifiable by a pattern of distributed blood vessels. However, the image processing in Japanese Unexamined Patent Publication No. 2006-239206 cannot effectively distinguish the blood vessels from the surrounding tissue, thus requiring comparison with a normal spectrum image for an appropriate diagnosis.

Therefore, an object of the present invention is to provide a sufficiently blood-vessel-enhanced image using white light illumination in an electronic endoscope system.

According to the present invention, an electronic endoscope system is provided that includes an RGB transformer, an R-signal amplifier, and a GB-signal amplifier.

The RGB transformer transforms image signals to RGB signals. The R-signal amplifier changes the amplitude of the R signals of the RGB signals to a predetermined gain value. The GB-signal amplifier nonlinearly changes the amplitude of the G and B signals of the RGB signals.

Furthermore, a signal processor for the electronic endoscope is provided that includes the RGB transformer, the R-signal amplifier, and the GB-signal amplifier.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
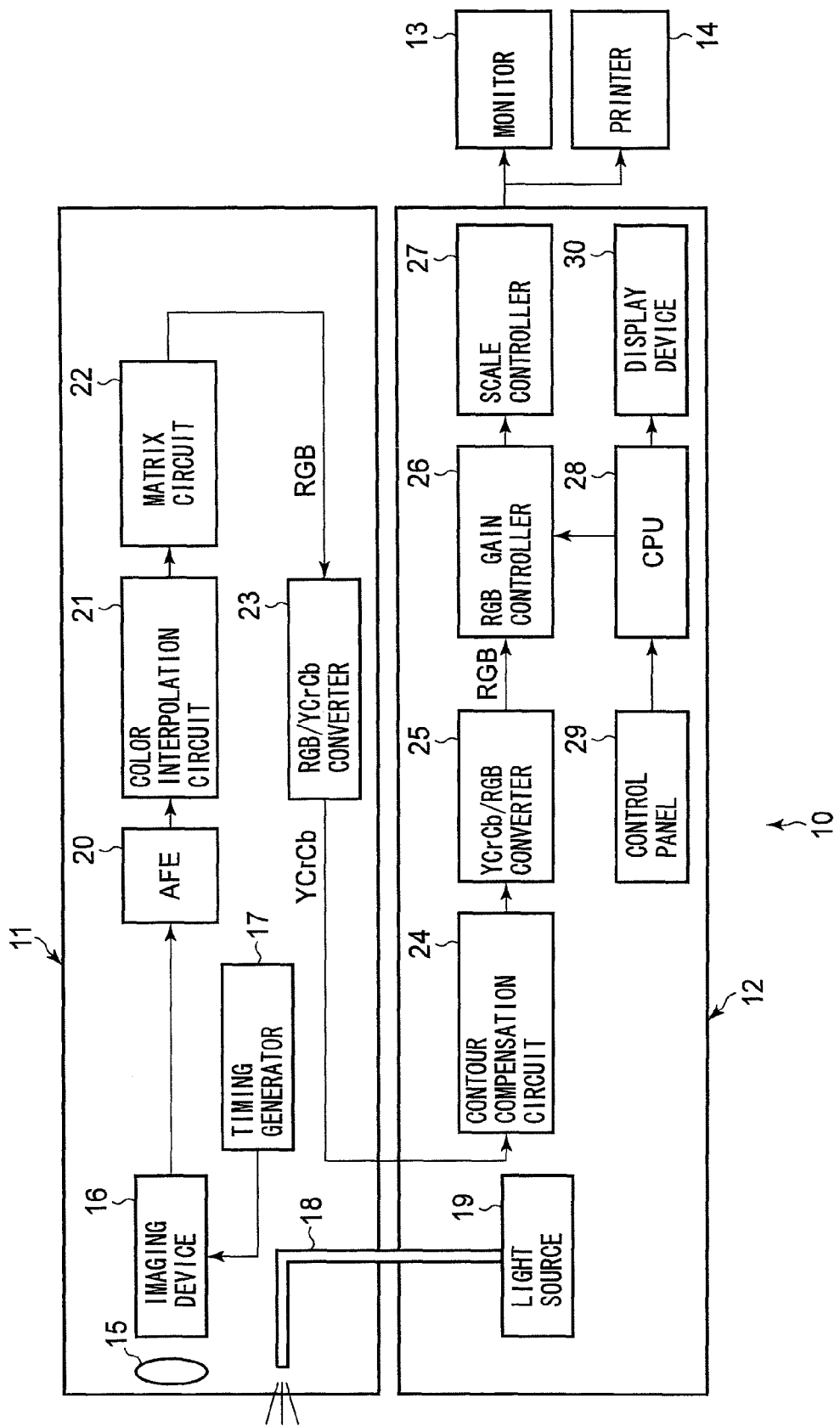
FIG. 1 is a block diagram of the electronic endoscope system of an embodiment of the present invention.

The present invention is described below with reference to the embodiments shown in the drawings.

FIG. 1 is a block diagram schematically illustrating the general structure of an electronic endoscope system of an embodiment to which the present invention is applied.

As is well know in the art, the electronic endoscope system 10 generally includes a scope portion 11 having a flexible tube for insertion into a body, a processing unit 12 to which the scope portion 11 is detachably attached and that receives image signals from the scope portion 11 to carry out image processing, and output device(s) such as a monitor 13 to display the images from the processing unit 12 and/or a printer 14 to record the images.

A photographic lens 15 and an imaging device 16 are provided at the distal end of the flexible tube of the scope portion 11. A timing generator 17, which may be provided inside the scope portion 11, drives the imaging device 16. The imaging device 16 captures images inside the body with white light, which may be supplied from a light source 19 provided inside the processing unit 12 through a light guide fiber 18.

The analog image signals of the RGB complementary colors obtained by the imaging device 16 are converted into digital image signals at an analog front end circuit 20 and then converted into the RGB signals through a color interpolation circuit 21 and a matrix circuit 22. The RGB signals are then converted into the YCrCb signals at an RGB/YCrCb converter 23 and fed to the processing unit 12.

The YCrCb signals, which are input to the processing unit 12 are then, for example, subjected to contour compensation at a contour compensation circuit 24 and converted into the RGB signals at a YCrCb/RGB converter 25. The RGB signals from the YCrCb/RGB converter 25 are amplified by an RGB gain controller 26 to predetermined gains (ratios), and are then fed to a scale controller 27. The RGB signals, which are amplified by the RGB gain controller 26, are subjected to size compensation that is carried out on the basis of the size of an image, and output to the monitor 13 or the printer 14.

The RGB gain controller 26 is connected to a CPU 28. The CPU 28 controls the RGB gain controller 26 in accordance with commands issued at keys provided on a control panel 29. Furthermore, a display device 30, such as an LCD monitor, is also connected to the CPU 28.

Figure 2:
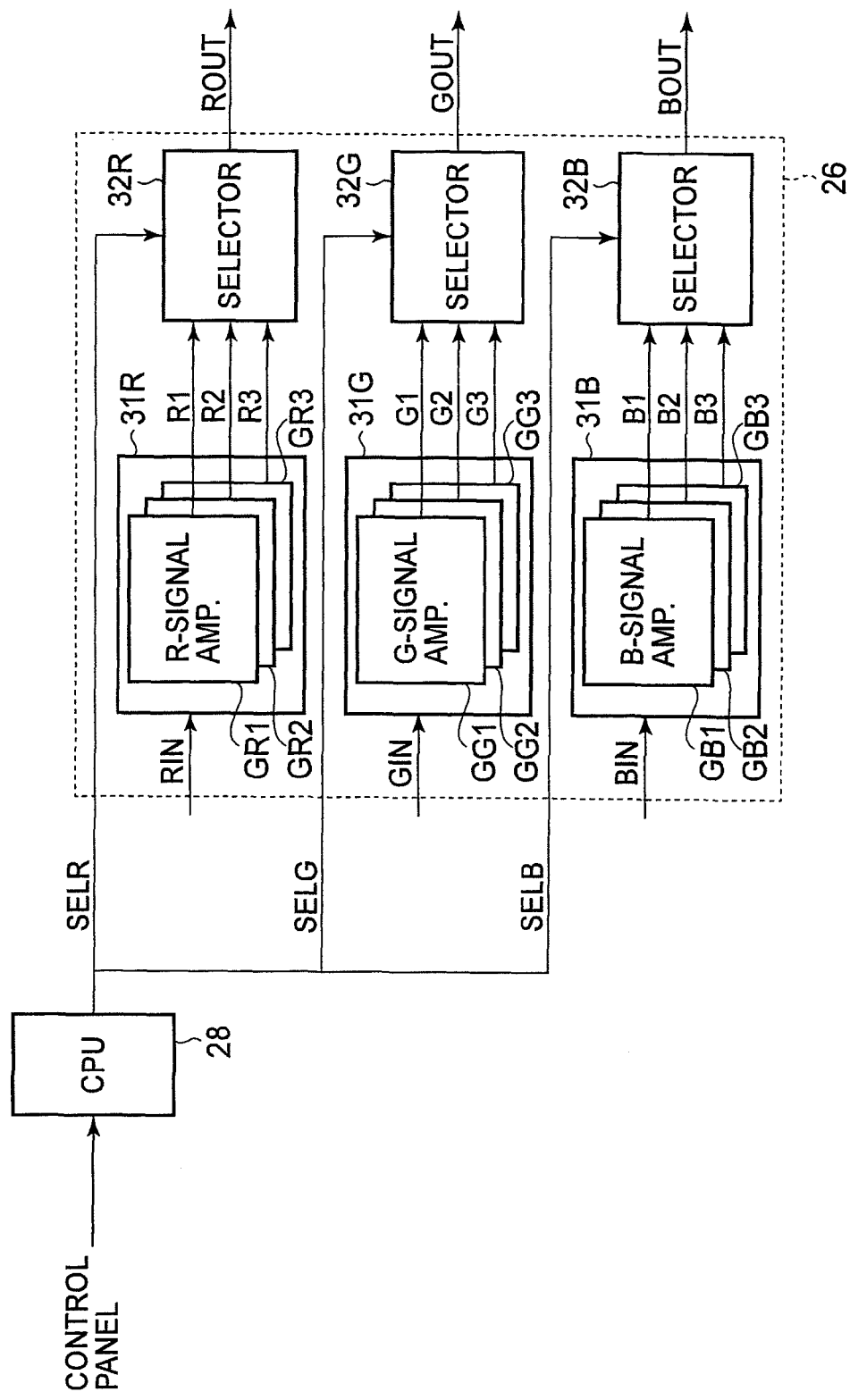
FIG. 2 is a block diagram of the RGB gain control unit illustrated in FIG. 1.
Figure 3:
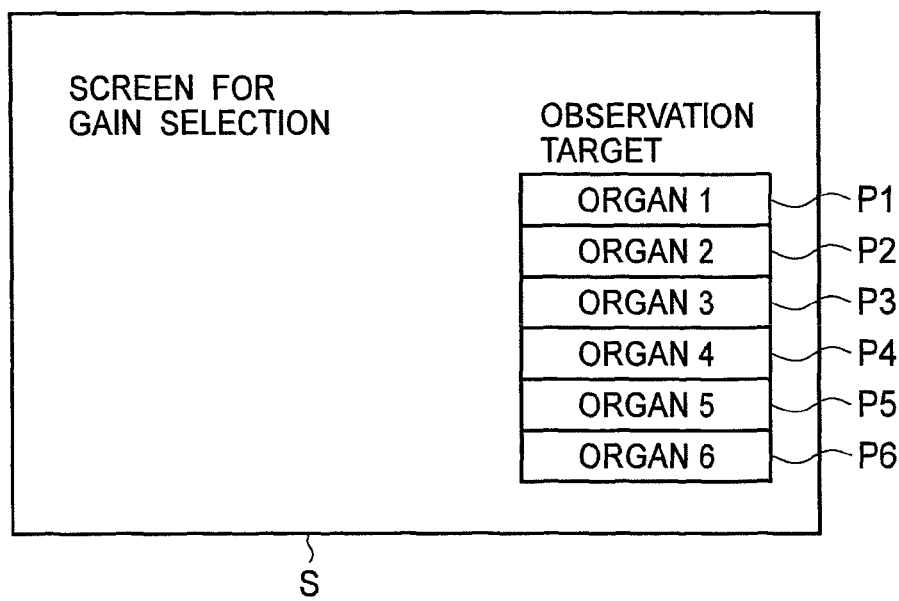
FIG. 3 is an example of the screen used to select the gain displayed on a display device.

With reference to FIGS. 2 and 3, structures and functions of the RGB gain controller 26 of the present embodiment will be explained. FIG. 2 is a block diagram giving the structural schematic of the RGB gain controller 26. FIG. 3 gives an example of an operational menu, i.e., a screen for selecting gain settings, displayed on the display device 30 for use in the control of the RGB gain controller 26.

The RGB gain controller 26 includes an R-signal amplifier 31R, G-signal amplifier 31G, and B-signal amplifier 31B that correspond respectively to R-signal RIN, G-signal GIN, and B-signal BIN input from the YCrCb/RGB converter 25. The R-signal amplifier 31R, G-signal amplifier 31G, and B-signal amplifier 31B, each has a plurality of amplifiers. In FIG. 2, three amplifiers GR1-GR3 for the R-signal amplifier 31R, three amplifiers GG1-GG3 for the G-signal amplifier 31G, and three amplifiers GB1-GB3 for the amplifier 31B are briefly illustrated. Note that when a mode for bypassing the blood vessel enhancement gain control is selected by key operation of the control panel 29, the amplifiers 31R, 31G, and 31B of the RGB gain controller 26 output RGB signals proportional to the input signals at the same gain.

In the present embodiment, the gain control for enhancing blood vessels in a target organ is carried out on each of the R, G, and B signals. As shown in FIG. 3, names of target organs are listed on the screen S of the display device 30 (such as "Organ 1", "Organ 2", ..., "Organ 6"; boxes P1-P6). Any of the boxes P1-P6 corresponding to a target organ may be selected by a user's key operation on the control panel 29. Examples of the target organs include the stomach, the intestines, the esophagus, and the lungs.

In the R-signal amplifier 31R, G-signal amplifier 31G, and B-signal amplifier 31B, the RGB gains are individually controlled to clearly enhance the blood vessels on the selected observation target organ. In the schematic of FIG. 2, the amplifiers GR1, GG1, and GB1 amplify the input signals RIN, GIN, and BIN, each at a gain suitable for the target organ 1, and in turn output the RGB signals R1, G1, and B1. In the same way, the amplifiers GR2, GG2, and GB2 amplify the input signals RIN, GIN, and BIN, respectively, at gains suitable for the target organ 2, and output the RGB signals R2, G2, and B2. Furthermore, the amplifiers GR3, GG3, and GB3 amplify the input signals RIN, GIN, and BIN, respectively, at gains suitable for the target organ 3, and output the RGB signals R3, G3, and B3.

The R-signals R1-R3 output from the R-signal amplifier 31R are input to a selector 32R, the G-signals G1-G3 output from the G-signal amplifier 31G are input to a selector 32G, and the B-signals B1-B3 output from the B-signal amplifier 31B are input to a selector 32B.

The selectors 32R-32B are controlled by selection signals SELR, SELG, and SELB, respectively. Namely, the selectors 32R-32B select a set of RGB signals adjusted to the target organ selected on the screen illustrated in FIG. 3 and output the RGB output signals ROUT, GOUT, and BOUT. For example, when the organ 1 is selected, the signals R1, G1, and B1 are selected by the selectors 32R, 32G, and 32B and the signals R1, G1, and B1 are output as the signals ROUT, GOUT, and BOUT. The aforementioned signals ROUT, GOUT, and BOUT are output to the scale controller 27.

The details of the gains set by the R-signal amplifier 31R, G-signal amplifier 31G, and B-signal amplifier 31B will be explained with reference to FIG. 4.

Figure 4:
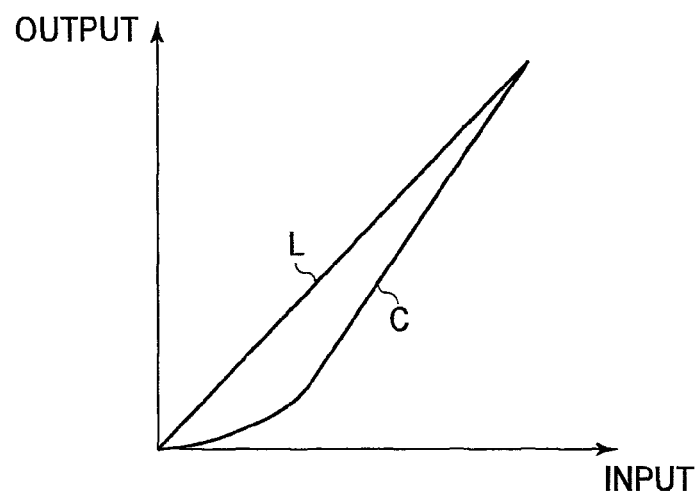
FIG. 4 is a graph that illustrates the gain (as a ratio) of the RGB signal outputs to the RGB signal inputs.

FIG. 4 is a graph that represents the relationship between the input signals RIN, GIN, and BIN and the output signals Rn, Gn, and Bn (n=1, 2, 3 for the example shown in FIG. 2) from the R-signal amplifier 31R, the G-signal amplifier 31G, and the B-signal amplifier 31B. The abscissa indicates the values of the input signals and the ordinate indicates the values of the output signals. In the present embodiment, the gains are controlled so as to enhance the blood vessels of the selected observation target (organ). For this enhancement, the output gain of the R-signal is set proportional to the input gain for all targets, as shown in FIG. 4. Namely, the R-signal gain is constant throughout the dynamic range as indicated by the straight line L in FIG. 4. However, the gains are set individually for each observation target (organ) such that different gain values may be set for different observation targets.

As for the G signals and the B signals, the value of gain varies in the dynamic range as indicated by curve C in FIG. 4. In particular, at the lower range of the input, the gains for the G signal and the B signal are set to comparatively low values compared to the value of the R-signal gain. The gains of the G signal and the B signal gradually increase as the input signal value increases and reach a value equal to the R-signal gain at the maximum value of the dynamic range. In the example of FIG. 4, the gains of the G signal and the B signal are represented by the same curve C, however, they can be set to different curves.

The gain G(x) for each signal input x (y=G(x)*x, where y represents the signal output) is preset in a memory device provided as a lookup table in each R-signal amplifier 31R, G-signal amplifier 31G, and B-signal amplifier 31B. In each amplifier, the gains are controlled by referring to the gain values stored in the memory devices.

In the present embodiment, the non-linear conversion of the RGB signals is carried out after the RGB conversion in the processing unit. However, the non-linear conversion may be carried out at any suitable time between the analog front-end process and the image display. Furthermore, although in the present embodiment, the selection of the observation target (organ) is carried out on the screen of the display device provided on the processing unit, the selection can be carried out on the screen of a computer system or the monitor used in the endoscopic system.

As described above, according to the present embodiment, an endoscopic image in which the blood vessels are enhanced is obtained with simple structures by adjusting the gains of the RGB signals, such that the gain for the R signal is linearly set and the G and B signals are set non-linearly. Furthermore, the user will not find it strange to compare the blood-vessel-enhanced image, i.e., the emulated spectral image, with the normal endoscopic image (without non-linear gain control), since the luminance and the color tone throughout the image are virtually unaltered by the blood-vessel enhancement or the spectral image emulation of the present embodiment.

Although the embodiment of the present invention has been described herein with reference to the accompanying drawings, obviously many modifications and changes may be made by those skilled in this art without departing from the scope of the invention.

The present disclosure relates to subject matter contained in Japanese Patent Application No. 2007-280030 (filed on Oct. 29, 2007), which is expressly incorporated herein, by reference, in its entirety.

The invention claimed is:

1. An electronic endoscope system, comprising:
    an endoscope for obtaining an image corresponding to an image signal;
    a processor detachably attached to the endoscope for receiving the image signal of the image and processing the image signal, the processor including;
        an RGB transformer that transforms the image signal into an R signal, a G signal, and a B signal, an R amplitude of the R signal, a G amplitude of the G signal, and a B amplitude of the B signal each existing within a dynamic range;
        an R-signal amplifier that changes the R amplitude of the R signal in accordance with a predetermined gain value throughout the dynamic range, the R-signal amplifier including a plurality of R-signal amplifiers; and
        a GB-signal amplifier that nonlinearly changes the G amplitude of the G signal and the B amplitude of the B signal throughout the dynamic range in accordance with a nonlinear function, the GB-signal amplifier including a G-signal amplifier that includes a plurality of G-signal amplifiers and a B-signal amplifier that includes a plurality of B-signal amplifiers;
    a display connected to the processor for receiving a processed image signal from the processor and displaying a processed image corresponding to the processed image signal;

a selector for selecting one of various observation targets to be observed, gains of the R-signal amplifier and the GB-signal amplifier being recorded as specific values for each of the various observation targets, the gains being selected according to the one of the various observation targets selected by the selector; and an output for outputting the R amplitude, the G amplitude, and the B amplitude from corresponding ones of the plurality of R-signal amplifiers, the plurality of G-signal amplifiers, and the plurality of B-signal amplifiers to the display in accordance with the one of the various observation targets selected by the selector, wherein each of the plurality of R-signal amplifiers changes the R amplitude of the R-signal in accordance with one of the various observation targets, each of the plurality of G-signal amplifiers changes the G amplitude of the G-signal in accordance with one of the various observation targets, each of the plurality of B-signal amplifiers changes the B amplitude of the B-signal in accordance with one of the various observation targets, and an R gain of the R signal equals a G gain of the G signal and a B gain of the B signal at limits of the dynamic range, with the G gain of the G signal and the B gain of the B signal increasing between the limits of the dynamic range.

2. The electronic endoscope system as claimed in claim 1, wherein the R gain of the R signal is greater than the G gain of the G signal and the B gain of the B signal between the limits of the dynamic range.

3. A signal processor for an electronic endoscope, comprising:

an RGB transformer that transforms an image signal into an R signal, a G signal, and a B signal, an R amplitude of the R signal, a G amplitude of the G signal, and a B amplitude of the B signal each existing within a dynamic range;

an R-signal amplifier that changes the R amplitude of the R signal in accordance with a predetermined gain value throughout the dynamic range, the R-signal amplifier including a plurality of R-signal amplifiers;

a GB-signal amplifier that nonlinearly changes the G amplitude of the G signal and the B amplitude of the B signal throughout the dynamic range in accordance with a nonlinear function, the GB-signal amplifier including a G-signal amplifier that includes a plurality of G-signal amplifiers and a B-signal amplifier that includes a plurality of B-signal amplifiers; and a determiner for determining one of various observation targets that is selected, gains of the R-signal amplifier and the GB-signal amplifier being recorded as specific values for the various observation targets, the gains being selected according to the one of the various observation targets that is selected, wherein the determiner further determines corresponding ones of the plurality of R-signal amplifiers, the plurality of G-signal amplifiers, and the plurality of B-signal amplifiers according to the one of the various observation targets that is selected, each of the plurality of R-signal amplifiers changes the R amplitude of the R-signal in accordance with one of the various observation targets, each of the plurality of G-signal amplifiers changes the G amplitude of the G-signal in accordance with one of the various observation targets, each of the plurality of B-signal amplifiers changes the B amplitude of the B-signal in accordance with one of the various observation targets, and an R gain of the R signal equals a G gain of the G signal and a B gain of the B signal at limits of the dynamic range, with the G gain of the G signal and the B gain of the B signal increasing between the limits of the dynamic range.

4. The signal processor as claimed in claim 3, wherein the R gain of the R signal is greater than the G gain of the G signal and the B gain of the B signal between the limits of the dynamic range.

* * * * *